(12) United States Patent
Jaworowski et al.

(10) Patent No.: US 10,571,388 B2
(45) Date of Patent: Feb. 25, 2020

(54) SYSTEM AND MATERIALS FOR CORROSION DETECTION

(71) Applicant: Sikorsky Aircraft Corporation, Stratford, CT (US)

(72) Inventors: Mark R. Jaworowski, Glastonbury, CT (US); Haralambos Cordatos, Colchester, CT (US); Lubomir A. Ribarov, West Hartford, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 723 days.

(21) Appl. No.: 15/110,931

(22) PCT Filed: Jan. 10, 2014

(86) PCT No.: PCT/US2014/011084
§ 371 (c)(1),
(2) Date: Jul. 11, 2016

(87) PCT Pub. No.: WO2015/105504
PCT Pub. Date: Jul. 16, 2015

(65) Prior Publication Data
US 2016/0334325 A1 Nov. 17, 2016

(51) Int. Cl.
*G01N 17/00* (2006.01)
*G01R 27/08* (2006.01)
*G01N 17/02* (2006.01)
*G01N 27/04* (2006.01)

(52) U.S. Cl.
CPC ........... *G01N 17/006* (2013.01); *G01N 17/02* (2013.01); *G01N 27/041* (2013.01); *G01R 27/08* (2013.01)

(58) Field of Classification Search
CPC .... G01N 17/006; G01N 17/02; G01N 27/041; G01R 27/08
USPC ......... 324/500, 600, 700, 200, 207.13, 529, 324/530, 71.1, 71.2, 219
See application file for complete search history.

(56) References Cited

U.S. PATENT DOCUMENTS

| | | | |
|---|---|---|---|
| 5,310,470 A | 5/1994 | Agarwala et al. | |
| 7,790,225 B1 | 9/2010 | Calle et al. | |
| 8,359,728 B2 | 1/2013 | Hefner et al. | |
| 2006/0019419 A1 | 1/2006 | Shin et al. | |
| 2009/0128169 A1 | 5/2009 | Fay et al. | |
| 2010/0206745 A1* | 8/2010 | Andreeva | B05D 5/00 205/766 |
| 2011/0210749 A1 | 9/2011 | Williams et al. | |
| 2013/0124109 A1* | 5/2013 | Denenberg | G01N 17/04 702/35 |

(Continued)

OTHER PUBLICATIONS

Feng, et al., "Smart Polymeric Coatings—Recent Advances", Advances in Polymer Technology, vol. 26, No. 1, 1-13, 2007, Wiley Periodicals, Inc.

(Continued)

*Primary Examiner* — Melissa J Koval
*Assistant Examiner* — Trung Nguyen
(74) *Attorney, Agent, or Firm* — Cantor Colburn LLP

(57) ABSTRACT

A system configured for detection of corrosion of a metal substrate is disclosed. The article includes a first layer disposed over the metal substrate comprising a first electrically conductive polymer, and a first electrical conductivity sensor in sensing contact with the first layer.

24 Claims, 3 Drawing Sheets

(56) References Cited

U.S. PATENT DOCUMENTS

2016/0041046 A1* 2/2016 Pagani ................... G01L 25/00
73/862.626

OTHER PUBLICATIONS

International Search Report for International Application No. PCT/US2014/11084; International Filing Date: Jan. 10, 2014; dated Apr. 25, 2014; 12 pages.

Li, et al, "Smart Coating for Corrosion Indication and Prevention: Recent Progress", downled from: http://ntrs.nasa.gov/archive/nasa/casi.ntrs.nasa.gov/20120003396_2012003780.pdf on Oct. 28, 2013; 18 pages.

Parajuli, Rishi R., "Developing Conducting Polymer Nanocomposites With Carbon Nanomaterials for Molecular Detection and Fuel Cell Applications", Rutgers University, Oct. 2011, Graduate School Disseration; 192 pages.

Written Opinion for International Application No. PCT/US2014/11084; International Filing Date: Jan. 10, 2014; dated Apr. 25, 2014; 6 pages.

* cited by examiner

SYSTEM AND MATERIALS FOR CORROSION DETECTION

CROSS REFERENCE TO RELATED APPLICATIONS

This application is a National Stage application of PCT/US2014/011084, filed on Jan. 10, 2014, the contents of which are incorporated by reference in their entirety herein.

BACKGROUND OF THE INVENTION

The subject matter disclosed herein generally relates to detection of metal corrosion, and more particularly to articles and methods that make use of electrically conductive polymer layers for detection of metal corrosion.

Metals of all sorts are used in a variety of applications where they are subject to corrosion. Some metals like iron and plain steel are inherently susceptible to corrosion. Other metals such as aluminum, magnesium, copper, and other alloys are more resistant to corrosion, but can nevertheless be susceptible to corrosion if they are subject to corrosive environments, as well as to galvanic corrosion if metals having different electrochemical potentials are used in proximity to or in contact with one another. Various techniques are used to try and prevent or reduce corrosion, including but not limited to protective coatings, corrosion-inhibiting pigments, and component material selection including the avoidance of galvanically incompatible materials as well as the use of sacrificial materials.

Regardless of the use and effectiveness of corrosion-inhibiting techniques, corrosion continues to be a challenge for metal components, presenting problems up to and including structural failure. Accordingly, it is beneficial if, in cases where corrosion occurs, it can be detected early so that counter measures can be taken or the corroding component replaced. However, in many applications, metal components can be covered by structures or coatings, or are otherwise difficult to view or access, such that detection of corrosion is difficult or delayed. Even when the components are readily accessible, physical inspection can be expensive, time-consuming, and unreliable. Accordingly, there continues to be a need for new alternatives for corrosion detection.

BRIEF DESCRIPTION OF THE INVENTION

According to some aspects of the invention, a system is configured for detection of corrosion comprises a metal substrate. This system comprises a first, electrically insulating, layer disposed over the metal substrate, a second layer comprising a first electrically polymer disposed over the first layer, and a first electrical conductivity sensor in sensing contact with the first layer. Corrosion of the metal substrate can be detected by detecting changes in the electrical conductivity or resistivity of the second layer. Of course, one need not measure conductivity or resistivity values if one only needs to monitor for changes in electrical conductivity; it is sufficient to measure a physical value that is proportional to conductivity or resistivity of the a material, such as the electrical conductance or resistance between two fixed locations in the layer. Therefore, as used herein, the term "electrical conductivity sensor" means a sensor that can detect changes in electrical conductivity, and, as such, the electrical conductivity sensor does not have to directly measure actual electrical conductivity of the material. Accordingly, the electrical conductivity sensor can actually be a sensor that measures electrical resistance or conductance between fixed locations in the layer.

In some aspects of the invention, the system comprises an electronic control unit (ECU) in communication with the first conductivity sensor. The ECU is configured to detect corrosion of the metal substrate based on a change in conductivity of the first electrically conductive polymer.

In some aspects of the invention, a third, electrically insulating, layer is disposed over the second layer, and a fourth layer comprising a second electrically conductive polymer is disposed over the third layer. The second electrically conductive polymer can be chemically the same as or different than the first electrically conductive polymer. A second electrical conductivity sensor is in sensing contact with the fourth layer. The output from the second electrical conductivity sensor can be used as a reference to compare against the output of the first electrical conductivity sensor in order to normalize the response to account for aging or environmental changes other than metal corrosion that can impact the electrical conductivity of both the first and layers.

In some aspects of the invention, a method of manufacturing a system configured for detection of corrosion of a metal substrate comprises adhering or otherwise securing a corrosion protection sensor over the metal substrate, and the corrosion detection sensor comprises the above-described second layer and first electrical conductivity sensor. The corrosion detection sensor can optionally include the third, electrically insulating, layer, and the fourth layer with second electrical conductivity sensor. In some aspects, a corrosion protection coating is applied to the metal substrate, followed by embedding, adhering or otherwise securing the corrosion detection sensor to the coated metal substrate. In some further aspects, the corrosion detection sensor is embedded, adhered, or otherwise secured before the corrosion protection coating has fully cured.

In some aspects of the invention, a corrosion detection sensor comprises an optional first electrically insulating layer, and a second layer comprising a first electrically conductive polymer and a first electrical conductivity sensor in sensing contact with the first layer. In some further aspects, the corrosion detection sensor further comprises a third, electrically insulating, layer disposed over the first layer, and a fourth layer disposed over the third layer comprising a second electrically conductive polymer that can be chemically the same as or different than the first electrically conducting polymer, and a second electrical conductivity sensor in sensing contact with the fourth layer.

In some aspects of the invention, a method of detecting corrosion of a metal comprises monitoring a second layer, disposed over a metal substrate and comprising a first electrically conductive polymer, for changes in electrical conductivity. A first, electrically insulating, layer is disposed between the metal substrate and the second layer. In some further aspects, a barrier (third) layer is disposed over the second layer, and a fourth layer comprising a second electrically conductive polymer, which can be the chemically the same as or different than the first electrically conductive polymer, is disposed over the barrier layer, and the method further comprises monitoring the second layer for changes in electrical conductivity. The results of the monitoring the fourth layer can be used as a reference against which to compare the results of monitoring the second layer.

In any individual or combination of the above-described aspects of the invention, either or both of the first and/or second electrically conductive polymers can have an electrical conductivity of at least 50 Siemens per centimeter (S/cm).

In any individual or combination of the above-described aspects of the invention, the first and/or second electrically conductive polymer can comprise a polymer backbone comprising conjugated double bonds.

In any individual or combination of the above-described aspects of the invention, the first and/or second electrically conductive polymer can be selected from the group consisting of substituted or unsubstituted: polydiphenylbenzidine, polyaniline, polypyrrole, polyacetylene, poly(p-phenylene vinylene), polyfluorene, polypyrene, polyazulene, polynaphthalene, polycarbazole, polyindole, polyazepine, polythiophene, poly(p-phenylene sulfide), poly(3,4-ethylenedioxythiophene), and mixtures comprising any of the foregoing.

In any individual or combination of the above-described aspects of the invention, the first layer can be a corrosion protection layer disposed on the metal substrate.

In any individual or combination of the above-described aspects of the invention, the second and/or fourth layer can include microcapsules that break down under conditions indicative of corrosion. The microcapsules can be made from electrically nonconductive polymers with functional groups that cause the microcapsule polymer to break down in the presence of conditions where corrosion is occurring (e.g., pH changes), thereby exposing electrically conductive material on the inside of the microcapsules to cause a detectable change in electrical conductivity of the layer. In some further aspects, the electrical conductivity of the material disposed in the microcapsules is different than the electrical conductivity of the layer outside the microcapsules. In some further aspects, the material in the microcapsules is an electrically conductive polymer, which may have an electrical conductivity different than the second layer outside of the microcapsules.

In any individual or combination of the above-described aspects of the invention, either or both of the electrical conductivity sensors can comprise two electrical leads disposed at separated locations in the electrically conductive polymer-containing layer, and the sensor(s) measure for changes in electrical conductivity by monitoring changes in electrical conductance or resistance between the electrical leads.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

It should be noted that, as used herein, the terms "over" and "under" are used with the perspective of the metal substrate being the lowest or bottom-most element, and are intended to describe the relationship of layers in direct contact with one another as well as layers with one or more other optional layers (not shown) interposed between a layer and another layer characterized as above or below it. For example, a layer described as over another layer would include aspects where the first-mentioned layer is directly on top of the other layer, and also aspects where the first-mentioned layer is positioned over the other layer with one or more additional layers positioned between the two layers. Although the invention is not bound by any particular theory or postulated mechanism of operation, it is believed that by-products or reaction conditions of metal corrosion reaction(s) can modify the electrical conductivity of a layer comprising an electrically conductive polymer, allowing for the detection of corrosion by monitoring for changes in the electrical conductivity of a layer comprising an electrically conductive polymer in proximity to a metal substrate. Such detection would be useful in a number of technologies, such as aircraft, naval vessels, buildings, or any other metallic structure whose corrosion needs to be monitored.

Figure 1:
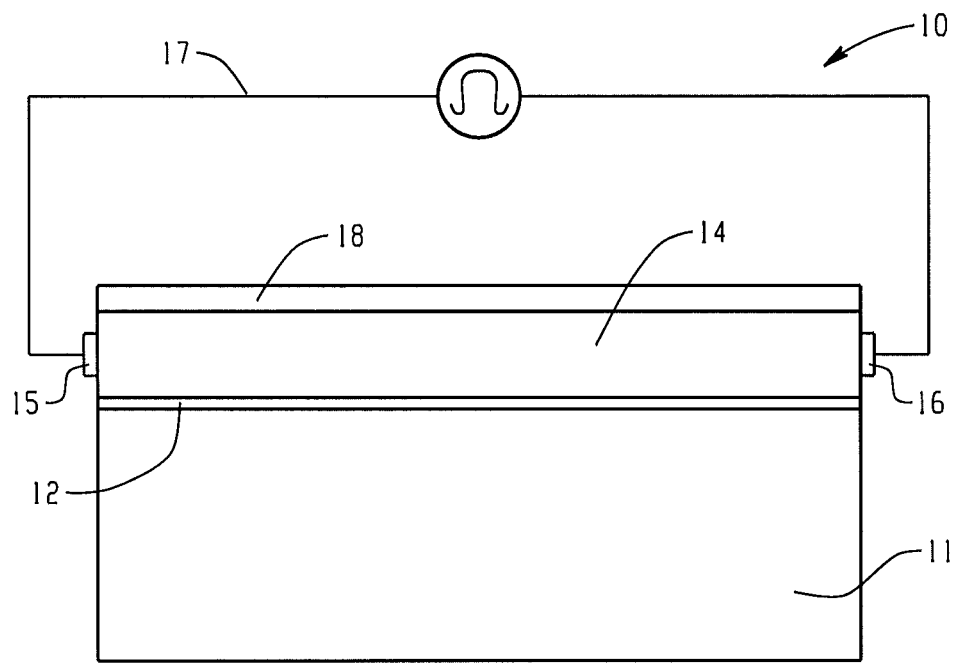
FIG. 1 schematically depicts an article as described herein having a single conductive polymer layer.

The invention is further described below in reference to the Figures. Referring now to FIG. 1, a system 10 configured for detection of corrosion in a metal substrate 11 is shown. As shown in FIG. 1, the metal substrate 11 has a first, electrically insulating, layer such as corrosion protection layer 12 disposed on the surface thereof, and a corrosion detection sensor comprising a second, conductive polymer, layer 14 disposed over corrosion protection layer 12. Electrical contacts 15 and 16 are in electrical contact with the first conductive polymer layer 14 at different locations, and are connected to circuitry 17 for monitoring electrical resistance between contacts 15 and 16 through the first conductive polymer layer 14. Circuitry 17 is shown connected to a separate ohmmeter (unnumbered, represented by the an Ω symbol inside a circle) associated with circuitry 17; however, in many cases both sets of circuitry 17 would connect wirelessly or hard-wired to an electronic control unit (ECU) and/or microprocessor that would receive and process the outputs of both sets of circuitry 17 to detect and/or alert for corrosion. For example, an ECU could compare measured electrical resistance against a predetermined limit resistance for triggering a corrosion warning, or could pre-programmed instructions to monitor for rates or patterns of change in electrical resistance. Corrosion protection layer 12 is optional, as the first, electrically insulating, layer can also be a metal oxide layer on the surface of metal substrate 11. The first, electrically insulating, layer helps to prevent electrical conductance paths between the electrical contacts 15 and 16 that go through the metal substrate 11. A topcoat layer 18 is disposed over the first conductive polymer layer 14. Such layers can be applied to any metallic substrate 11, such as an aircraft part, such as by being coated onto the metal substrate 11 or by affixing a corrosion sensor comprising the above-described layers onto the metal substrate 11, in aspects of the invention.

Figure 2:
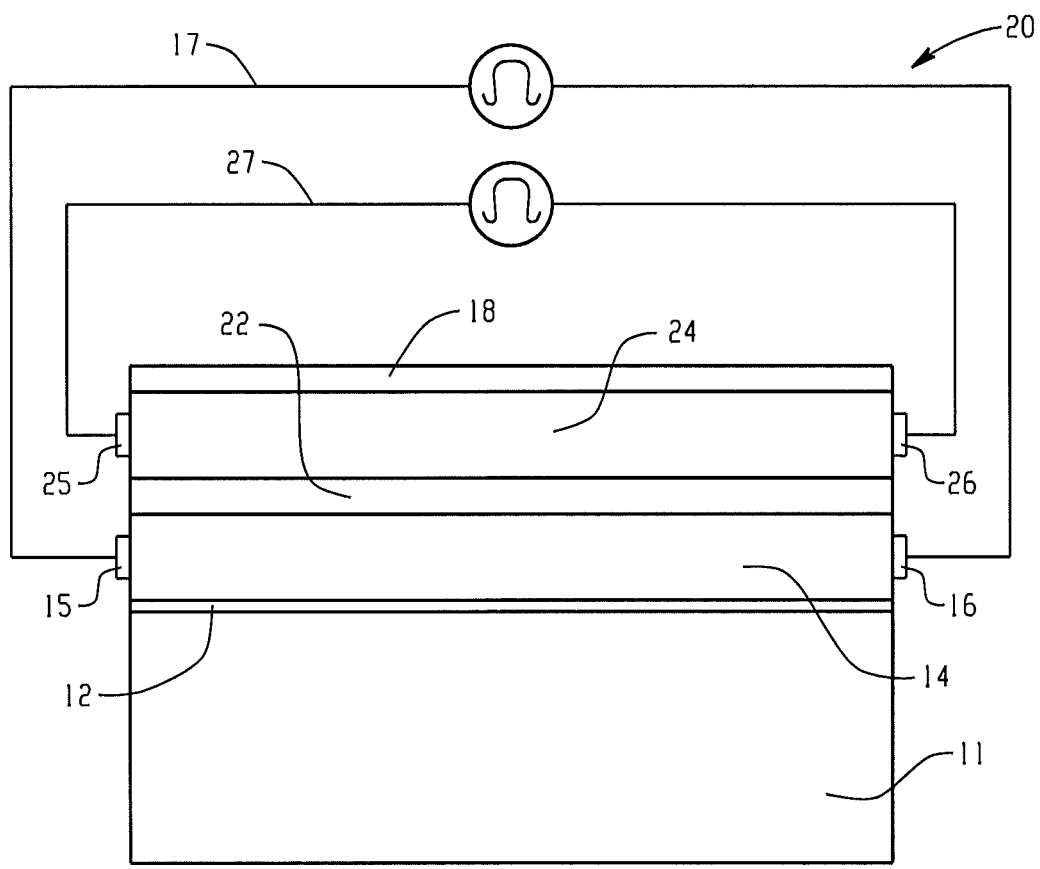
FIG. 2 schematically depicts an article as described herein having two conductive polymer layers.

Turning now to FIG. 2, a system 20 configured for detection of corrosion in the metal substrate 11 is shown. As shown in FIG. 2, the metal substrate 11 has the optional corrosion protection layer 12 disposed on the surface thereof, and a corrosion detection sensor comprising the conductive polymer layer 14 disposed over the corrosion protection layer 12. Electrical contacts 15 and 16 are in electrical contact with the conductive polymer layer 14 at different locations, and are connected to circuitry 17 for monitoring electrical resistance between contacts 15 and 16 through the conductive polymer layer 14. A third, electrically insulating, layer 22 such as an electrically insulating polymer is disposed over the second electrically conductive layer 14, and a fourth, electrically conductive, polymer layer 24 is disposed over the third layer 22. Electrical contacts 25 and 26 are in electrical contact with the conductive polymer layer 24 at different locations, and are connected to circuitry 27 for monitoring electrical resistance between contacts 25 and 26 through the conductive polymer layer 24. As with the FIG. 1 system, circuitry 17, 27 is shown connected to a separate ohmmeter associated with circuitry 17; however, in many cases both sets of circuitry 17, 27 would connect to an electronic control unit (ECU) and/or microprocessor that would receive and process the outputs of both sets of circuitry 17, 27 as described above. In order to monitor for situations where the presence of other causes of variation of electrical conductivity of the electrically conducting layer 14 besides corrosion of the metal substrate 11 (e.g., humidity-induced variations, temperature-induced variations, aging, etc.), the results provided by circuitry 17 can be compared to the results provided by circuitry 27 to distinguish changes in electrical conductivity caused by corrosion, which would tend to affect the electrical conductivity of electrical conductive polymer layer 14, compared to changes in electrical conductivity caused by other factors, which would tend to affect the electrical conductivity of both electrically conducting polymer layers 14 and 24. A topcoat layer 18 is disposed over the fourth conductive polymer layer 24.

Figure 3A:
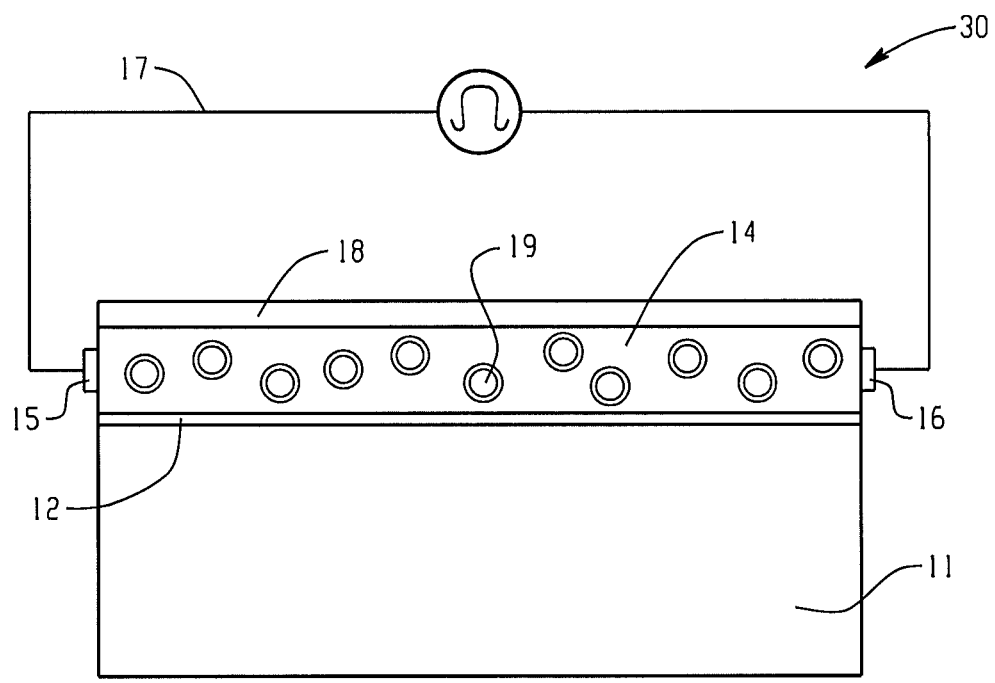
FIGS. 3A and 3B schematically depict an article as described herein with a layer having conductive polymer disposed in microcapsules that break down under conditions indicative of corrosion.
Figure 3B:
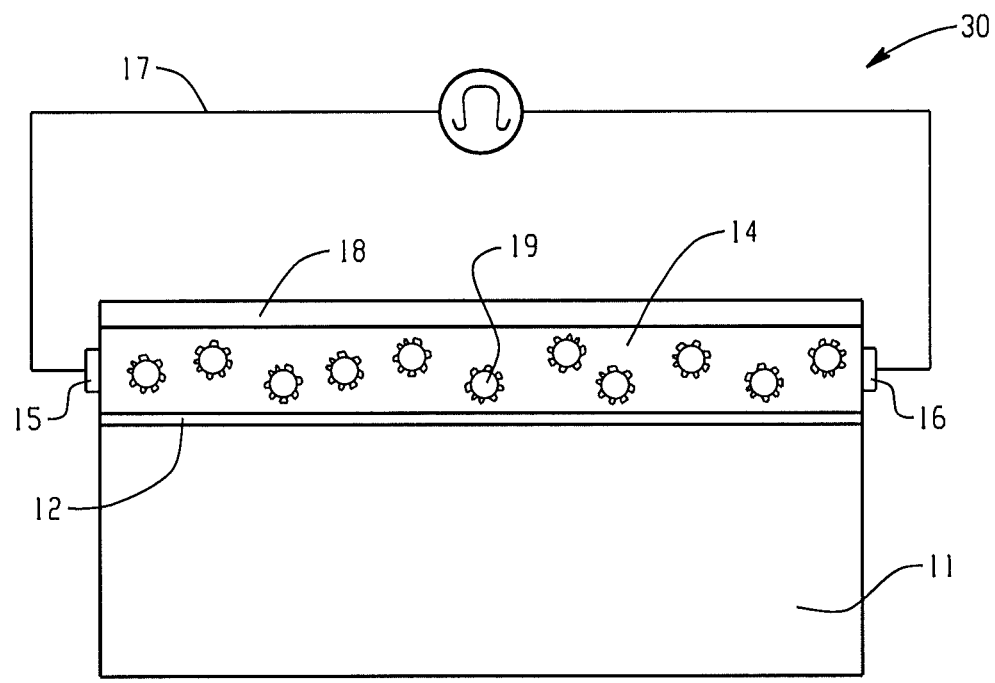

Turning now to FIG. 3, FIG. 3A depicts a system 30 configured for detection of corrosion in the metal substrate 11. As shown in FIG. 3A, the metal substrate 11 has corrosion protection the layer 12 disposed on the surface thereof, and a corrosion detection sensor comprising conductive polymer layer 14 disposed over corrosion protection layer 12. Electrical contacts 15 and 16 are in electrical contact with the conductive polymer layer 14 at different locations, and are connected to circuitry 17 for monitoring electrical resistance between contacts 15 and 16 through the conductive polymer layer 14. A topcoat layer 18 is disposed over the conductive polymer layer 14. Electrically conductive polymer layer 14 further includes a plurality of microcapsules 19 containing electrically conducting material. The electrically conducting material in the microcapsules 19 can be an electrically conducting polymer that is chemically the same as or different from the electrically conducting polymer outside of the microcapsules 19. In some embodiments, the electrically conducting polymers on the inside and the outside of the microcapsules 19 are different, which allows for the two polymers and their different electrically conductive and other properties to be selected so as to provide a desired response to indicia of corrosion. FIG. 3A depicts the system 30 in the absence of corrosion where the microcapsules 19 are intact. The microcapsules 19 comprise nonconductive polymer shells, and in FIG. 3A they act to reduce the area for electrical pathways between the electrical contacts 15 and 16 through the conductive polymer layer 14, which tends to increase resistance between the electrical contacts 15 and 16. FIG. 3B depicts the system 30 where corrosion of the metal substrate 11 has caused the breakdown or disintegration of the microcapsules 19, thus exposing the electrically conducting polymer inside the microcapsules 19 and increasing the conductive pathways through the electrically conductive polymer layer 14, which tends to reduce the measured electrical resistance between the electrical contacts 15 and 16, in addition to the effect(s) from corrosion on the electrical conductivity of the electrically conducting polymer.

Figure 4:
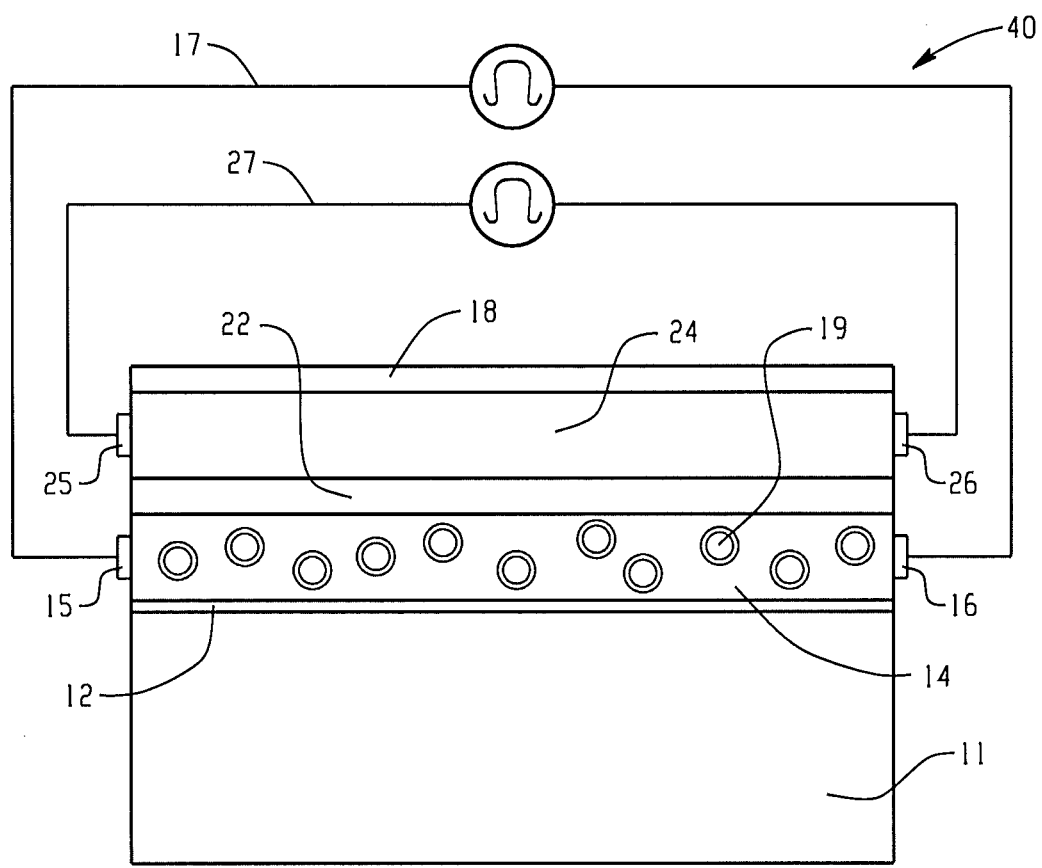
FIG. 4 schematically depicts an article as described herein with a layer having conductive polymer disposed in microcapsules that break down under conditions indicative of corrosion and a second conductive polymer layer.

Turning now to FIG. 4, which combines some of the features of FIGS. 2 and 3, a metal article 40 comprises a metal substrate 11 having a first corrosion protection layer 12 disposed on the surface thereof, and a corrosion detection sensor comprising first conductive polymer layer 14 disposed over corrosion protection layer 12. Electrical contacts 15 and 16 are in electrical contact with the first conductive polymer layer 14 at different locations, and are connected to circuitry 17 for monitoring electrical resistance between contacts 15 and 16 through the second conductive polymer layer 14. Second electrically conductive polymer layer 14 further includes a plurality of microcapsules 19 containing electrically conducting material. The electrically conducting material in the microcapsules 19 can be chemically the same as or different from the electrically conducting polymer outside of the microcapsules 19. In some embodiments, the electrically conducting polymers on the inside and the outside of the microcapsules 19 are different, which allows for the two polymers and their different electrically conductivity and other properties to be selected so as to provide a desired response to indicia of corrosion. A third barrier layer 22 such as an electrically insulating polymer is disposed over the second electrically conductive layer 14, and a fourth electrically conductive polymer layer 24 is disposed over the barrier layer 22. Electrical contacts 25 and 26 are in electrical contact with the fourth conductive polymer layer 24 at different locations, and are connected to circuitry 27 for monitoring electrical resistance between contacts 25 and 26 through the fourth conductive polymer layer 24. A topcoat layer 18 is disposed over the fourth conductive polymer layer 24.

Various electrically conductive polymers can be used in the layer(s) described herein. In some aspects, the electrically conductive polymers include those with conjugated double bonds in the polymer backbone, which can provide molecular electron distributions conducive to conducting. In some aspects the electrically conductive polymer is a microporous material such as a zeolite, covalent organic framework, metal organic framework. The conjugated double bonds can be in aromatic rings integrated into the polymer backbone, or in unsaturated straight chain groupings. Examples of electrically conducting polymers include, but are not limited to poly(3,4-ethylenedioxythiophene): poly(styrene sulfonic acid) ("PEDOT:PSS"), polydiphenylbenzidine, polyaniline, polypyrrole, polyacetylene, poly(p-phenylene vinylene), polyfluorene, polypyrene, polyazulene, polynaphthalene, polycarbazole, polyindole, polyazepine, polythiophene, poly(p-phenylene sulfide), poly (3,4-ethylenedioxythiophene), and mixtures comprising any of the foregoing. The selection of electrically conductive polymer used for any of the conductive polymer layers described herein can be influenced by the corrosion indicator being monitored for. For example, protonatable nitrogen-containing electrically conductive polymers like polydiphenylbenzidine, linear polyethyleneimine ("L-PEI"), poly-o-phenylenediamine ("PoPD") are known to demonstrate changes in electrical conductivity as its nitrogen atoms become protonated, and protons can be an indicator of corrosion. The conductive polymer can also be a grafted copolymer, a composite of conductive polymer particles in a polymer matrix, and can be compounded as either a printable ink or an organic coating. In some embodiments, the electrically conductive polymer(s) can have an electrical conductivity of at least 50 Siemens per centimeter (S/cm), more particularly at least 100 S/cm, and even more particularly at least 200 S/cm. Upper limits for electrical conductivity of the electrically conductive polymer(s) can be 1000

S/cm, more particularly 500 S/cm. The electrical resistance of the conductive polymer elements can be measured by AC methods or at a multiplicity of DC bias values to detect and correct for the non-linear voltage/current relationship obtained by parasitic ionic conduction. Electrically conductive polymers generally do not exhibit thermoplastic properties, so the electrically conductive polymer layers are typically formed from coating composition dispersions in a liquid solvent using coating techniques known in the art.

Polymers used for microcapsules in any of the layer(s) described above can be, for example, polymers with groups that cause the microcapsule wall to break down or disintegrate under conditions associated with corrosion such as extreme pH (e.g., a pH of 9 or higher, 4 or lower). Such shell polymers can include, for example, polymers having ester or thioester linkages that are subject to hydrolysis at high pH. The microcapsules can be formed by forming micro-emulsions of the desired size distribution and forming the polymer capsule through interfacial polymerization, as described e.g. by U.S. Pat. No. 7,790,225, the disclosure of which is incorporated herein by reference.

The layers, such as the corrosion protection layer 12, the barrier layer 22, and the topcoat layers 18, 28 can be formed from various electrically insulating materials such as thermoplastic or thermoset polymers such as polyurethanes, acrylic polymers, phenolics, epoxies, etc., which are well known in the art such that they do not require additional detailed explanation herein. Crosslinking agents such as melamine resin can be included to enhance layer integrity. The layers can be applied as coating composition dispersions in a solvent (including water or organic solvents), or where applicable as thermoplastic compositions heated to a melt flow state. In some exemplary embodiments, non-polymeric materials can also be used. For example, an electrically insulating ceramic can be used to form the barrier layer 22, although such may present different manufacturing challenges than using polymer layers. Non-polymeric corrosion protection coatings such as trivalent chromium coatings well-known in the art as TCP can be used as a corrosion protection coating. In some embodiments, the system(s) described herein can be built up layer by layer with successive coatings. In some embodiments, the electrically conductive polymer layer(s) and conductivity sensor(s) can be fabricated together as a corrosion detection sensor and then secured over a metal surface. For example, a corrosion detection sensor comprising an electrically conductive polymer layer and a conductivity sensor can be adhered or otherwise secured to a metal substrate coated with an electrically insulating layer. In some embodiments, a corrosion detection sensor with or without its own electrically insulating layer can be placed onto metal substrate having an uncured or partially cured electrically insulating coating such as a corrosion protection coating so that the corrosion detection sensor is embedded or partially embedded in the coating or adhered to the surface of the coating as it is cured. In some embodiments, a corrosion detection sensor corrosion having its own electrically insulating layer can be adhered or otherwise secured directly to a metal surface.

The embodiments described herein can be used to monitor corrosion on virtually any type of component or article that contains metal that may be subject to corrosion. Corrosion can be monitored locally or remotely, and the corrosion monitoring can be integrated into various process or system management schemes, such as on-board vehicle monitoring systems such as an on-board Health Usage and Monitoring System (HUMS) as can be found onboard some commercial aircraft, as well as providing regular updated downloads for component/system maintenance programs.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. By way of example, while shown using electrodes 15, 16, it is understood that wireless mechanisms could be used to detect the conductivity, such as using an RFID and RFID tags to detect the change in conductivity without having wires connected between the circuitry 17 and/or 27 and the polymer layers 14 and/or 24. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A system configured for detection of corrosion a metal substrate, the system comprising:
    a first, electrically insulating, layer disposed on a surface of the metal substrate;
    a second layer disposed over the first layer with the first layer between the second layer and the metal substrate, the second layer comprising a first electrically conductive polymer; and
    a first conductivity sensor in sensing contact with the second layer, which detects a change in conductivity of the first electrically conductive polymer due to corrosion of the metal substrate, wherein the first conductivity sensor comprises a first electrical lead in electrical contact at a first location of the second layer, a second electrical contact at a second location of the second layer, and circuitry connected to the first and second electrical contacts configured to monitor for changes in electrical resistance through the second layer between the first and second locations.

2. The system of claim 1, comprising an electronic control unit in communication with the first conductivity sensor, configured to detect corrosion of the metal substrate based on the output of the first conductivity sensor.

3. The system of claim 1, wherein the first electrically conductive polymer has an electrical conductivity of at least 50 S/cm.

4. The system of claim 1, wherein the first electrically conductive polymer comprises a polymer backbone comprising conjugated double bonds.

5. The system of claim 1, wherein the first electrically conductive polymer is selected from the group consisting of substituted or unsubstituted: polydiphenylbenzidine, polyaniline, polypyrrole, polyacetylene, poly(p-phenylene vinylene), polyfluorene, polypyrene, polyazulene, polynaphthalene, polycarbazole, polyindole, polyazepine, polythiophene, poly(p-phenylene sulfide), poly(3,4-ethylenedioxythiophene), and mixtures comprising any of the foregoing.

6. The system of claim 1, wherein the first layer is a corrosion protection layer disposed on the metal substrate.

7. The system of claim 1, wherein the second layer comprises microcapsules that break down under conditions indicative of corrosion, and that contain an electrically conductive material.

8. The system of claim 7, wherein the electrically conductive material disposed in the microcapsules has an electrical conductivity that is different than that of the layer on the outside of the microcapsules.

9. The system of claim 1, further comprising
a third, electrically insulating, layer disposed over the second layer;
a fourth layer disposed over the second layer, comprising a second electrically conductive polymer that can be the chemically the same as or different than the first electrically conductive polymer; and
a second conductivity sensor conductivity sensor in sensing contact with the fourth layer, which detects a change in conductivity of the second electrically conductive polymer due to corrosion of the metal substrate.

10. The system of claim 9, comprising an electronic control unit in communication with the first and second conductivity sensor, configured to detect corrosion of the metal substrate based on the output of the first and second conductivity sensors.

11. The system of claim 9, wherein the second electrically conductive polymer has an electrical conductivity of at least 50 S/cm.

12. The system of claim 9, wherein the second electrically conductive polymer comprises a polymer backbone comprising conjugated double bonds.

13. The system of claim 9, wherein the second electrically conductive polymer is selected from the group consisting of substituted or unsubstituted: polydiphenylbenzidine, polyaniline, polypyrrole, polyacetylene, poly(p-phenylene vinylene), polyfluorene, polypyrene, polyazulene, polynaphthalene, polycarbazole, polyindole, polyazepine, polythiophene, poly(p-phenylene sulfide), poly(3,4-ethylenedioxythiophene), and mixtures comprising any of the foregoing.

14. The system of claim 9, wherein the fourth layer comprises microcapsules that break down under conditions indicative of corrosion, and that contain an electrically conductive material.

15. The system of claim 14, wherein the electrically conductive material disposed in the microcapsules in the fourth layer has an electrical conductivity that is different than that of the layer on the outside of the microcapsules.

16. The system of claim 9, wherein the second conductivity sensor comprises a third electrical lead in electrical contact at a first location of the fourth layer, a fourth electrical contact at a second location of the fourth layer, and circuitry connected to the third and fourth electrical contacts configured to monitor for changes in electrical resistance through the fourth layer between the first and second locations.

17. The system of claim 9, wherein the second electrically conductive polymer is chemically the same as the first electrically conductive polymer in the first layer.

18. A method of manufacturing the system of claim 1, comprising adhering or otherwise securing a corrosion protection sensor to the metal surface, the corrosion protection sensor comprising said second layer and said first electrical conductivity sensor.

19. The method of claim 18, further comprising applying a corrosion protection coating to the metal substrate, and embedding, adhering, or otherwise securing the corrosion protection sensor to the coated metal surface.

20. The method of claim 19, wherein the corrosion protection sensor is embedded, adhered, or otherwise secured to the coated metal surface prior to complete curing of the corrosion protection coating.

21. A corrosion detection sensor, comprising
a first, electrically insulating, layer;
a second layer comprising a first electrically conductive polymer, wherein the first layer is between the second layer and a metal substrate; and
a first conductivity sensor in sensing contact with the first layer, which detects a change in conductivity of the first electrically conductive polymer due to corrosion of the metal substrate, wherein the first conductivity sensor comprises a first electrical lead in electrical contact at a first location of the second layer, a second electrical contact at a second location of the second layer, and circuitry connected to the first and second electrical contacts configured to monitor for changes in electrical resistance through the second layer between the first and second locations.

22. The corrosion detection sensor of claim 21, comprising the first, electrically insulating, layer.

23. The corrosion detection sensor of claim 21, further comprising:
a third, electrically insulating, layer disposed over the second layer;
a fourth layer disposed over the third layer, comprising a second electrically conductive polymer that can be chemically the same as or different than the first electrically conductive polymer; and
a second electrical conductivity sensor in sensing contact with the fourth layer, which detects a change in conductivity of the second electrically conductive polymer due to corrosion of the metal substrate.

24. A method of detecting corrosion of a metal, comprising:
monitoring a second layer comprising an electrically conductive polymer for changes in electrical conductivity, said second layer being disposed over a first, electrically insulating, layer, the first layer being disposed over the metal, wherein monitoring the second layer comprises monitoring for changes in electrical resistance between a first location of the second layer and a second location of the second layer via a circuitry having a first electrical lead in electrical contact with the first location and a second electrical lead in electrical contact with the second location.

* * * * *